United States Patent
Reisberg et al.

(12) 
(10) Patent No.: US 6,423,068 B1
(45) Date of Patent: Jul. 23, 2002

(54) METHOD AND APPARATUS FOR MANDIBULAR OSTEOSYNTHESIS

(76) Inventors: Erhard Reisberg, Auf dem Graben #3, 79019 Staufen (DE); Brian S. Schumacher, 2338 Millford Lane West, Jacksonville, FL (US) 32246

( * ) Notice: Subject to any disclaimer, the term of this patent is extended or adjusted under 35 U.S.C. 154(b) by 0 days.

(21) Appl. No.: 09/152,706

(22) Filed: Oct. 18, 2000

(51) Int. Cl.$^7$ ............................................... A61B 17/58
(52) U.S. Cl. .................................................. 606/69
(58) Field of Search ............................ 606/60, 69, 70, 606/71, 151

(56) References Cited

U.S. PATENT DOCUMENTS 1,105,105 A * 7/1914 Sherman
4,966,599 A * 10/1990 Pollock ...................... 606/69
5,690,631 A * 11/1997 Duncan et al. ............... 606/69

* cited by examiner

Primary Examiner—David O. Reip
(74) Attorney, Agent, or Firm—Harness, Dickey & Pierce, P.L.C.

(57) ABSTRACT

An apparatus for osteosynthesis of a mandible. An elongated plate has a plurality of apertures. The plate has a first portion, a second portion, and a central portion intermediate the first and second portions. Each of the apertures within the first portion and within the second portion are disposed in relatively close spaced relationship, and each of the apertures within the central portion are disposed in relatively widely spaced relationship. The width of the plate between apertures is less in the central portion than in the first portion. The plate is more easily bent within the central portion than within the first portion, and can be bent to a relatively small radius in the central portion without distorting the apertures within the central portion. The central portion is sized and located to overlie the symphysis of the mandible.

34 Claims, 3 Drawing Sheets

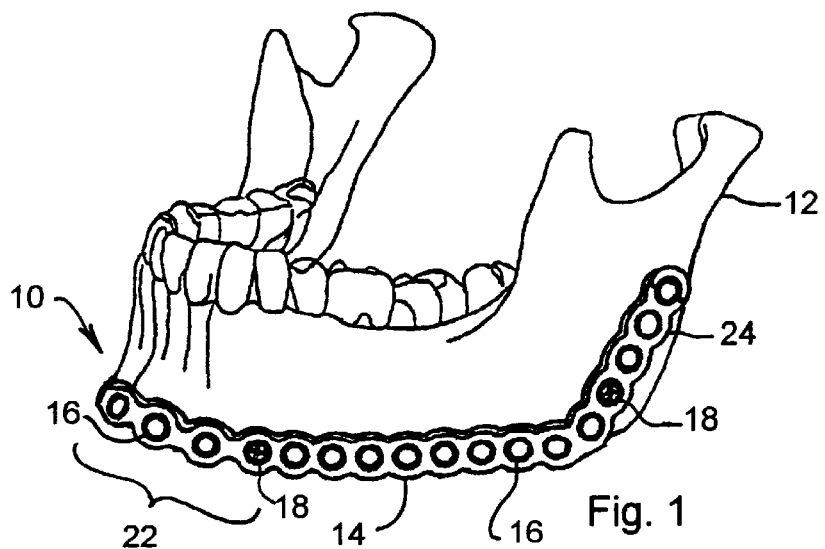
Fig. 1
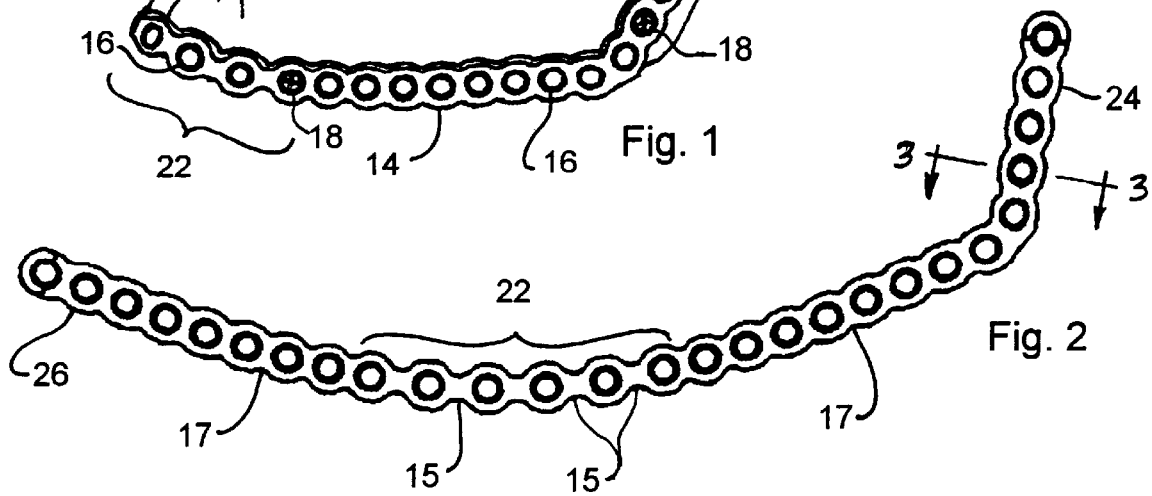
Fig. 2
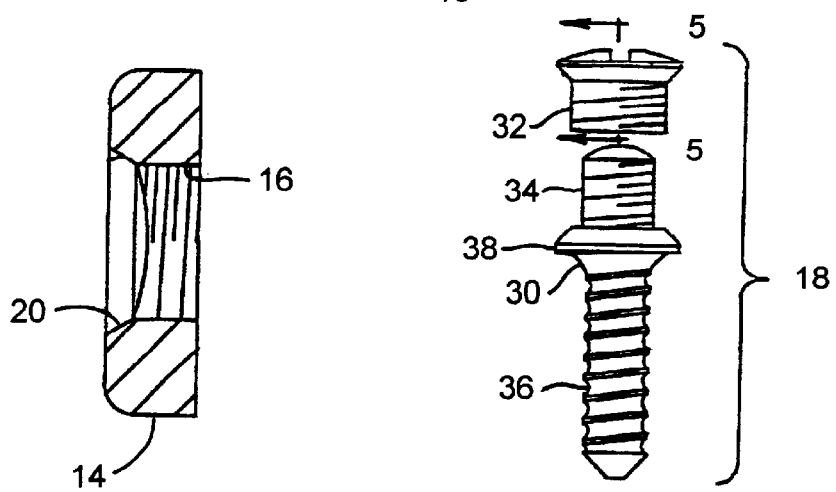
Fig. 3
Fig. 4

METHOD AND APPARATUS FOR MANDIBULAR OSTEOSYNTHESIS

BACKGROUND OF THE INVENTION

1. Field of the Invention

The present invention relates to surgical repair of fractures, deformities, diseases and surgical osteotomies of bone. More particularly, the present invention relates to a method and apparatus for mandibular osteosynthesis.

2. Discussion of the Related Art

In various craniofacial surgical procedures, it is necessary to align and secure two bone portions in a relatively fixed relationship to each other. As examples, the need to establish such a secured relationship can arise from a fracture of the bone or from an oncology resection of the bone. To ensure that the bone can regenerate in the proper orientation and fuse the fracture, or maintain mandibular shape after an oncology resection, it is important that the bone portions be fixed in the desired position.

It is known in the art to provide metal plates for the repair of bone fractures. Such plates generally are secured to bone portions with fasteners, especially screws. Among other applications, such plates and fasteners are used to provide rigid stabilization of craniofacial fractures and oncology resections. The plates conventionally employed for cranial and facial osteosynthesis generally comprise small, generally flat, elongated sections of metal. The plate sections contain round and perhaps elongated screw holes at various points along their lengths for receiving screws to fasten the plate sections to bone.

Because no surface of the human skeleton is completely flat, existing plates must be extensively twisted, formed and bent during surgery to conform to portions of the skeleton on which they are to be affixed. Significant time is expended during surgery shaping and re-shaping metal plates to conform adequately to bone surfaces. This expenditure of time increases anesthesia requirements and operating room time and also increases the potential for infection.

In one commonly used technique for mandibular reconstruction, an initially flat plate is bent to conform to the contours of the surface of the mandible. The conformed plate is secured to the mandible by a plurality of screw fasteners received through holes in the plate. The screw fasteners penetrate into and gain purchase in the bone. Subsequently, the fasteners and plate are removed to allow surgical access to the mandible, e.g., to remove a cancerous growth. Finally, the plate is fastened again to the mandible by engaging the fasteners with the previously formed holes in the mandible.

While known systems utilizing plates and fasteners for cranial and facial osteosynthesis have proven to be acceptable for certain applications, such systems are nevertheless susceptible to improvements that may enhance their performance. Known systems do not provide plates having enhanced screw placement options together with enhanced bending ease at desired locations, while preserving the integrity of screw holes at bending sites and avoiding interference between screws in adjacent screw holes. These and other desirable improvements are provided by the present invention, preferred embodiments of which are described below with reference to the drawings.

SUMMARY OF THE PRESENT INVENTION

According to one aspect of the present invention, an apparatus for osteosynthesis of a mandible includes an elongated plate having a plurality of apertures. The plate has a first portion and a central portion. Each of the plurality of apertures within the first portion and within the second portion is disposed in relatively close spaced relationship, and each of the plurality of apertures within the central portion is disposed in relatively widely spaced relationship.

According to another aspect of the present invention, a method of surgically repairing a mandible includes the step of providing an elongated plate having a plurality of apertures, the plate having a first portion and a central portion. Each of the plurality of apertures within the first portion is disposed in relatively close spaced relationship, and each of the plurality of apertures within the central portion is disposed in relatively widely spaced relationship. A further step includes providing a fastener having means for engaging the mandible and having means for engaging an aperture of the plate. Yet a further step includes securing the elongated plate to the mandible with the fastener. Another step includes bending the plate to substantially conform to the mandible such that the central portion overlies the symphysis of the mandible.

It is an object of the present invention to provide an osteosynthesis plate for use in surgical repair of a mandible having enhanced bending ease in the vicinity of the symphysis of the mandible.

It is a further object of the present invention to provide an osteosynthesis plate for use in surgical repair of a mandible that presents enhanced options for screw placement outside the vicinity of the symphysis of the mandible.

It is yet a further object of the present invention to provide an osteosynthesis plate for use in surgical repair of a mandible that permits bending of the plate to a relatively small radius in the vicinity of the symphysis of the mandible while preserving the boundary integrity of the apertures in the area of bending.

Additional objects and advantages of the present invention will be apparent from the descriptions below of preferred embodiments and their methods of use, made with reference to the drawings.

BRIEF DESCRIPTION OF THE DRAWINGS

FIG. 1 is a perspective view of a mandibular osteosynthesis system constructed in accordance with the present invention, illustrated in operative association with a human mandible.

FIG. 2 is an illustration of the locking plate shown in FIG. 1 according to the teachings of the present invention.

FIG. 3 is a cross-sectional view taken along the line 3—3 of FIG. 2.

FIG. 4 is an exploded view of one of the fasteners shown in FIG. 1 according to the teachings of the preferred embodiment of the present invention.

DETAILED DESCRIPTION OF THE PRESENT INVENTION

Figure 5:
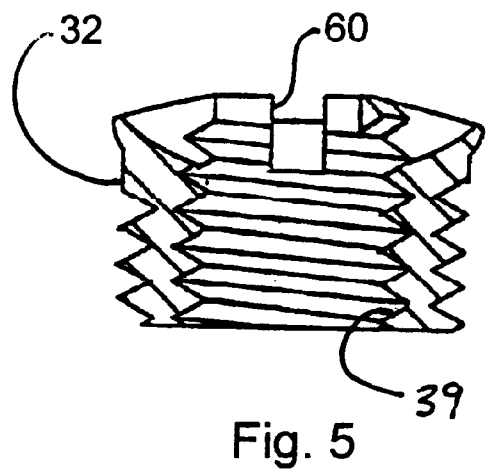
FIG. 5 is a cross-sectional view taken along the line 5—5 of FIG. 4.

The following description of the preferred embodiments of the present invention is merely exemplary in nature and is in no way intended to limit the invention or its application or uses.

Referring to FIG. 1, a system constructed in accordance with a preferred embodiment of the present invention is generally identified by reference numeral 10. The system 10 is shown operatively associated with a human mandible 12. However, it will become apparent to those skilled in the art that certain aspects of the present invention have applicability to other bones of the skeleton and other surgical procedures.

With continued reference to FIG. 1 and with reference to FIGS. 2, 3 and 4, the system 10 of the present invention is shown to include an elongated plate 14 and a plurality of fasteners 18. The plate 14 is formed to include a plurality of apertures 16, each adapted to receive a fastener 18 for interconnecting the plate 14 with the mandible 12. Each aperture 16 preferably includes an oval countersink 20 and is internally threaded. As described further below, the internal threading of apertures 16 permits locking of fastener 18 to plate 14. For this reason, plate 14 is also referred to herein as a locking plate 14.

The locking plate 14 is shown to include generally a central portion 22, and first and second ends 24 and 26. The first end 24 is precontoured to conform generally to the shape of the posterior portion of the mandible 12 near the temporal mandibular joint. The central portion 22 and the second end 26 also are precontoured such that plate 14 can be bent around the anterior portion, or symphysis, of mandible 12 and lie adjacent the side of mandible 12 opposite to that side of mandible 12 to which first end 24 lies adjacent. The central portion 22 of plate 14, after bending, lies adjacent the symphysis. Prior to bending, second end 26 may be regarded as curving superiorly in a sagittal plane relative to central portion 22.

At the first and second ends 24 and 26, respectively, and in next adjacent regions of plate 14, the plurality of apertures 16 of plate 14 are disposed in relatively close spaced relationship. In contrast, in the central portion 22 of plate 14, intended to be bent intraoperatively to lie adjacent to the symphysis, the plurality of apertures 16 are disposed in relatively widely spaced relationship. In the central portion 22, regions 15 of plate 14 that are disposed between next adjacent apertures 16, are narrower in width than are regions 17 of plate 14 that are disposed between next adjacent apertures located outside central portion 22. The narrower, or necked, regions 15, in combination with the wider spacing of the nearby apertures 16, make plate 14 more easily bendable in central portion 22. More particularly, plate 14 is more susceptible to being bent, and being bent to a greater degree, between holes in the central portion 22 than outside the central portion 22. This arrangement facilitates bending of plate 14 in the region of the symphysis, where the natural contour of the bone dictates that the plate 14 be bent more severely than in other regions to conform to the contour of the bone.

In one application, the locking plate 14 is constructed of titanium. More preferably, the locking plate 14 is constructed of commercially pure, Grade 2 or Grade 4 titanium. However, it will be appreciated by those skilled in the art that other materials having suitable performance and biocompatibility characteristics may be employed. Preferably, the locking plate 14 is inelastically deformable so as to retain its shape once contoured to conform to the shape of the mandible 12.

Figure 6:
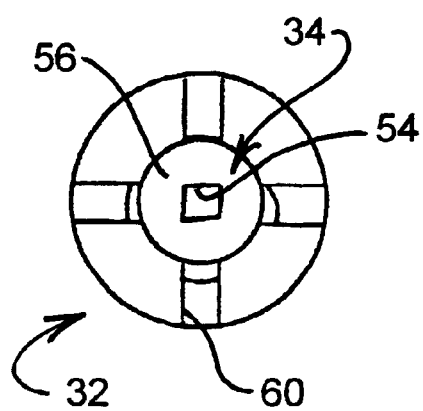
FIG. 6 illustrates an end view of the head of the fastener shown in FIG. 4 according to the present invention.

With reference to FIGS. 4–6, the fastener 18 of the present invention is shown to generally include a main body 30 and a head member 32. The main body 30 includes an upper shaft portion 34 and a lower shaft portion 36. The lower shaft portion 36 is externally threaded and adapted to penetrate and engage the mandible or bone 12 in a conventional manner. Insertion of the lower shaft portion into the bone is limited by a flange 38 interposed between the upper and lower shaft portions 34 and 36. The upper shaft portion 34 is externally threaded and adapted to engage an internally threaded aperture 39 of the head member 32. The head member 32 is externally threaded for engaging one of the plurality of internally threaded apertures 16 of the locking plate 14.

In one application, the thread pitches of the upper shaft portion 34, lower shaft portion 36 and the external threads of the head member 32 are common. The external threads of the head member 32 and the externally threaded lower shaft portion 36 have a common thread lead. In the exemplary embodiment illustrated, the externally threaded lower shaft portion 36 has a single lead configuration while the external threads of the upper shaft portion 34 and head member 32 have a double lead configuration.

In use, a malleable template (not shown) is positioned on the mandible 12 and bent to the general shape of the adjacent bone surface. Next, the locking plate 14 is bent to approximately the shape of the template and positioned on the mandible 12 so that certain apertures 16 may be selectively used as a guide for drilling holes (not specifically shown) in the mandible 12 for receiving the fasteners 18. The bending is generally more severe around the symphysis, or chin area. It is desirable to bend the plate between the apertures to maintain the integrity of the internal threads of the apertures. A first one of the fasteners 18 is passed through a selected one of the apertures 16 and rotated so that the externally threaded lower portion 36 engages and is driven into the hole in the mandible 12. For example, the first end 24 of the locking plate 14 may be secured first to the mandible 12 with a first fastener 18. As the externally threaded lower portion 36 of the fastener 18 is driven into the bone 12, the external threads of the head member 32 eventually engage the internally threaded aperture 16 of the locking plate 14 and advance simultaneously with the external threads of lower portion 36. This is possible as a result of the common thread lead shared between the lower portion 36 and the head member 32.

Additional fasteners 18 are used to interconnect the locking plate 14 with the bone 12 in a substantially identical manner. As shown in FIG. 1, four fasteners are used to interconnect the locking plate 14 with the bone 12. However, it will be appreciated by those skilled in the art that any number of fasteners 18 may be employed depending on a particular application. As each fastener is engaged with the bone 12, the locking plate 14, previously having been bent to conform to the shape of the mandible, is drawn into its operative position adjacent to the bone 12.

At this point of the surgical procedure, the head members 32 of each of the threaded fasteners 18 are unthreaded from their respective upper portions 34. This allows the surgeon to remove the locking plate 14 from the fasteners 18 and displace the locking plate 14 from the bone. This provides access to the bone 12 for accomplishing a desired surgical procedure, e.g., removal of a cancerous growth. The lower portions 36 of fasteners 18 remain embedded in the bone. When the locking plate 14 is removed, it retains its shape due to its inelastic deformation. When the surgical procedure is complete, the locking plate 14 is replaced by inserting the upper portions 34 of the fasteners 18 through the respective apertures 16 and simultaneously engaging the internal threads of the head members 32 with the external threads of the upper portion 34, and the external threads of the head member 32 with the internal threads of the aperture 16. Since the fasteners 18 are not removed from the bone 12 after initial insertion, fastener-to-bone purchase is not compromised.

Figure 7:
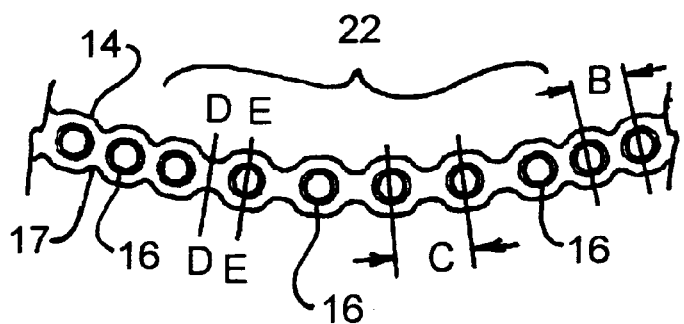
FIG. 7 is a detail illustration of the embodiment of the locking plate of FIG. 2.

With reference to FIG. 7, a detail view is shown of central portion 22 of plate 14 and next adjacent regions of plate 14 outside of central portion 22. Outside of central portion 22, the plurality of apertures 16 are evenly spaced along plate 14, having a preferred center to center spacing, B, of less than about 0.34 inches, and a most preferred center to center spacing of about 0.295 inches. The regions 17 between adjacent apertures 16 outside of central portion 22 have a preferred width in the plane of plate 14 of about 0.18 to about 0.32 inches, and a most preferred width of about 0.20 inches to about 0.24 inches. Within central portion 22, the plurality of apertures 16 also is evenly spaced along plate 14, but at a wider spacing than that of the apertures 16 outside of central portion 22. The preferred center to center spacing, C, of apertures 16 is greater than about 0.39 inches, and as most preferred, about 0.411 inches, within central portion 22. Within central portion 22, the regions 15 between adjacent apertures 16 have a preferred width in the plane of plate 14 of about 0.12 inches to about 0.22 inches, and a most preferred width of about 0.16 inches. Plate 14 has a substantially constant thickness over its entire length in the range of about 0.06 inches to about 0.12 inches, with most preferred thicknesses of about 0.079 or about 0.102 inches. Each of apertures 16 has a diameter of about 0.10 inches to about 0.18 inches, and a most preferred diameter of about 0.16 inches. As preferred, the major diameter of oval countersink 20 is about 0.211 inches, and the minor diameter of oval countersink 20 is about 0.188 inches. The cross-sectional area of plate 14 taken in a transverse plane D—D in region 15 between adjacent widely spaced apertures in central portion 22 is less than the cross-sectional area of plate 14 taken in a transverse plane E—E diametrically across an aperture 16. With a preferred plate thickness of about 0.079 inches, the preferred cross-sectional area in plane D—D is about 0.0126 square inches and the preferred total cross-sectional area in plane E—E is about 0.014 square inches. Alternatively, with a preferred plate thickness of about 0.102 inches, the preferred cross-sectional area in plane D—D is about 0.016 square inches and the preferred total cross-sectional area in plane E—E is about 0.018 square inches.

In central region 22, the increased center-to-center spacing of apertures 16, together with the reduced width of region 15 between adjacent apertures, and further in combination with the lesser cross-sectional area of plate 14 in regions 15 relative to the cross-sectional area of plate 14 through apertures 16, results in certain advantages over the prior art. More specifically, enhanced ease of bending of plate 14 is provided in central portion 22, with the bending occurring between adjacent apertures 16 with little or no distortion of the plate 14 surrounding each aperture 16. The prevention of distortion of the boundaries of apertures 16 is particularly advantageous in that the internal threading and circularity of apertures 16 is preserved, thereby ensuring that apertures 16 are able to receive fasteners 18 therethrough even after plate 14 has been bent in central portion 22 to conform to the shape of the adjacent mandible bone. The increased spacing between adjacent apertures in central portion 22 is further advantageous in that it alleviates interference between the shanks of fasteners 18 received through adjacent apertures 16 in central portion 22 in the case where central portion 22 has been bent to a relatively small radius to conform to the symphysis of the mandible.

The location of central portion 22, and the total length of central portion 22, is chosen to ensure that some part of central portion 22 will fall on the symphysis of the mandible in about 90% of adult patients. To conform to the mandible, plate 14 must be bent to a smaller radius in the vicinity of the symphysis than in the vicinity of other portions of the mandible. As preferred, the total length of central portion 22 is about 2.35 inches. Central portion 22 starts about 2.50 inches from the sharp angular transition in plate 14 near the first end 24.

Figure 8:
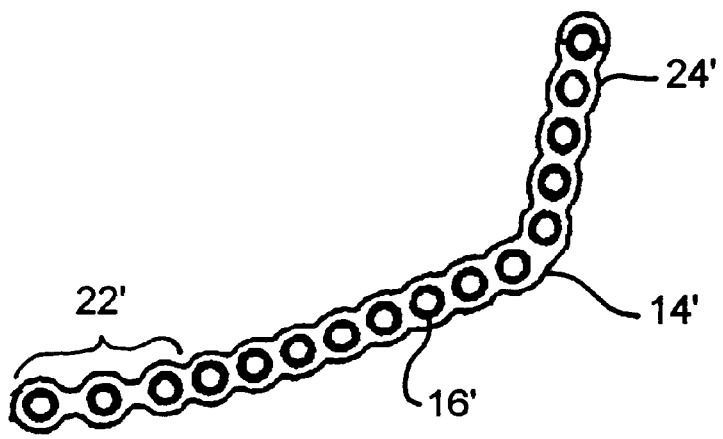
FIG. 8 is an illustration of an alternative embodiment of a locking plate configured according to the present invention.
Figure 9:
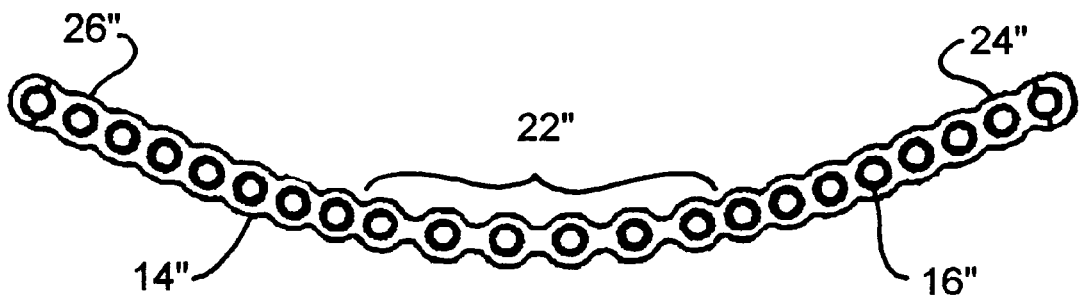
FIG. 9 is an illustration of yet another alternative embodiment of a locking plate configured according to the present invention.

With reference to FIGS. 8 and 9, alternative embodiments are shown of a locking plate constructed in accordance with the present invention. Portions of the alternative embodiments corresponding to previously described embodiments are indicated by like primed or double primed reference numerals. In FIG. 8, plate 14' is truncated in the center of central portion 22, having no second end 26. Plate 14' is useful in surgical applications in which it is known that the locking plate 14' need not extend past the centerline of the symphysis. In FIG. 9, plate 14" is useful is surgical applications in which it is known that the locking plate need not extend superiorly toward the temporal mandibular joint. Any of plates 14, 14' and 14" can be cut to any desired length intraoperatively to accommodate the surgical procedure. Other possible embodiments (not shown) would include apertured plates generally similar to plates 14, 14' and 14", in which the plate is initially straight rather than having a preformed curve. With such straight plates, the desired curve would be formed intraoperatively.

Figure 10:
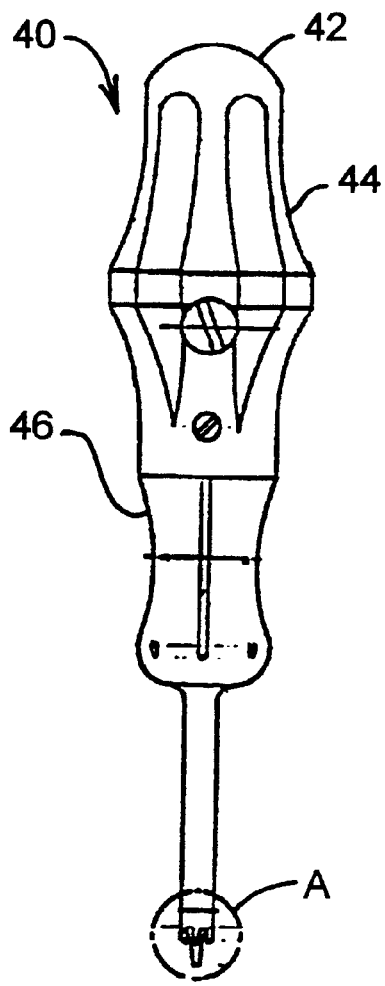
FIG. 10 is an illustration of a tool useful in connection with the mandibular osteosynthesis system of the present invention.
Figure 11:
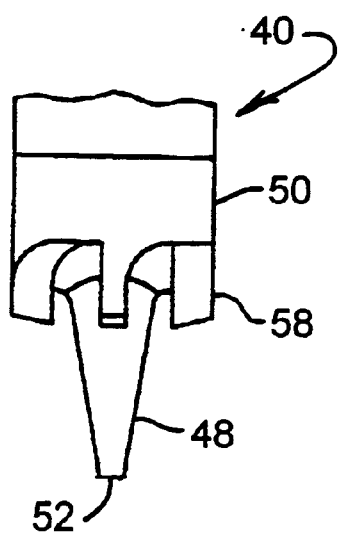
FIG. 11 is an enlarged view illustrating the detail shown in circle A identified in FIG. 10.
Figure 12:
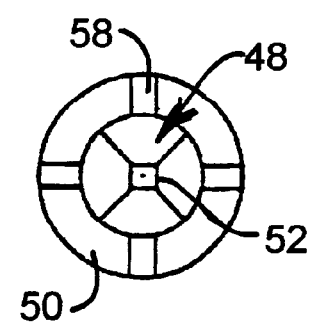
FIG. 12 is an enlarged end view of the tool shown in FIG. 14.

With reference to FIGS. 10–12, one suitable tool for use in connection with the system 10 of the present invention is shown and generally identified with reference numeral 40. The tool includes a handle 42 having an upper portion 44 and a lower portion 46. The upper and lower portions 44 and 46 are rotatable relative to one another about the longitudinal axis of the tool 40. The upper portion 44 is adapted to rotate together with a first drive portion 48, while the lower portion 46 of the handle 42 is adapted to rotate together with a second drive portion 50.

With continued reference to FIGS. 10"12, and further reference to FIGS. 5–6, the first drive portion 48 includes a generally rectangular tip 52 adapted to engage a generally rectangular aperture 54 provided in a top surface 56 of the upper shaft portion 34 of each fastener 18. The second drive portion 50 is illustrated to include four drive elements generally equally spaced about the first drive member 48. The drive elements 58 are adapted to engage a corresponding number of slots 60 equally spaced about the head member 32 of each fastener 18.

After the holes are drilled into the mandible 12, the surgeon selects a fastener with the head portion 32 threaded onto the upper shaft portion 34 of the main body 30 and engages the drive elements 58 of the tool 40 with the slots 60 of the head member 32. Simultaneously, the tip 52 of the drive member 48 engages the rectangular aperture 54 of the upper shaft portion 34. The surgeon grasps the upper and lower portions 44 and 46 of the handle 42 and rotates the tool 40 in a conventional manner. This action causes the head member 32 to threadedly engage an aperture 16 of locking plate 14 and simultaneously causes the threads of the lower shaft portion 36 of the fastener 18 to engage the hole provided in the bone 12.

Once all of the fasteners 18 are initially inserted into the bone 12, the surgeon again engages the drive elements 58 with the head 32. The thumb and forefinger are used to rotate the lower portion 46 of the handle 42 and in turn to rotate the head portion 32 of the fastener 18 in a counterclockwise direction. Simultaneously, the palm and remaining fingers grasp the upper portion 44 of the handle 42 so that the lower portion 46 can be rotated relative thereto. This action removes the head member 32 from its aperture 16. Since the main body portion 30 of the fastener 18 is not simultaneously rotated, the head portion 32 is unthreaded therefrom. In a similar manner, after the desired surgical procedure is performed on the mandible 12, the head portion 32 is returned to threaded engagement with both the aperture 16 of the plate 14 and the upper shaft portion 32 of the main body portion 30. When the locking plate 14 is operatively associated with the mandible 12 as shown in FIG. 1, the locking plate 14 is adjacent to but slightly displaced from the bone 12. In this regard, the flange 38, which is, interposed between the upper and lower externally threaded portions 34 and 36 of the fasteners 18 limits downward translation of the removable head member 32. The thickness of the head member 32 is greater than the thickness of the locking plate 14. As a result, when a head member 32 is completely threaded on to the upper portion 34 of an associated fastener 18, the head member 32 extends beyond the locking plate 14 toward the bone and the locking plate 14 is displaced from the bone 12. Such spacing reduces resorption of the bone that otherwise might occur if the locking plate 14 were to contact the bone 12 directly.

In the preferred embodiment, the fasteners 18 are constructed from titanium 6AL4V alloy. However, it will be appreciated by those skilled in the art that other materials of having suitable strength and biocompatible characteristics may be incorporated.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention. For example, the configuration of the locking plate 14 shown in the drawings is one example of a locking plate suitable for use with the teachings of the present invention. Those skilled in the art will understand that various other shapes may be employed. For example, the locking plate 14 may be straight, angled, curved or any combination thereof. In certain applications, the locking plate 14 may extend about the entire mandible 12.

We claim:

1. An apparatus for osteosynthesis of a mandible comprising:
an elongated plate having a plurality of apertures, said plate having a portion A, a portion B, and a portion C, each of said plurality of apertures within said portion A and within said portion B being disposed in relatively close spaced relationship, and each of said plurality of apertures within said portion C being disposed in relatively widely spaced relationship, wherein said plate between next adjacent apertures within said portion A has a first width, and said plate between next adjacent apertures within said portion C has a second width, said second width being substantially less than said first width.

2. The apparatus of claim 1, in which said first width is about 0.18 inches to about 0.32 inches, and said second width is about 0.12 inches to about 0.22 inches.

3. The apparatus of claim 2, in which each of said apertures has a diameter of about 0.10 to about 0.18 inches.

4. The apparatus of claim 2, in which each of said apertures has a diameter of about 0.16 inches.

5. The apparatus of claim 1, in which said first width is about 0.20 inches to about 0.24 inches, and said second width is about 0.12 inches to about 0.22 inches.

6. The apparatus of claim 1, in which said first width is about 0.20 inches and said second width is about 0.16 inches.

7. The apparatus of claim 1, in which said plate is more easily bent within said portion C than within said portion A.

8. The apparatus of claim 7, in which said plate, diametrically transverse across one of said apertures, has a first total cross-sectional area, and said plate, transverse between next adjacent apertures within said portion C, has a second cross-sectional area less than said first total cross-sectional area.

9. The apparatus of claim 7, in which said relatively close spaced relationship is less than about 0.34 inches center to center, and said relatively widely spaced relationship is greater than about 0.39 inches center to center.

10. The apparatus of claim 7, in which said relatively close spaced relationship is a distance of about 0.295 inches center to center between adjacent apertures, and said relatively widely spaced relationship is a distance of about 0.411 inches center to center between adjacent apertures.

11. The apparatus of claim 7, in which said portion C has a length greater than about 1.0 inches and said portion A has a length greater than about 1.0 inches.

12. The apparatus of claim 1, in which said relatively close spaced relationship is less than about 0.34 inches center to center, and said relatively widely spaced relationship is greater than about 0.39 inches center to center.

13. The apparatus of claim 1, in which said relatively close spaced relationship is a distance of about 0.295 inches center to center between adjacent apertures, and said relatively widely spaced relationship is a distance of about 0.411 inches center to center between adjacent apertures.

14. The apparatus of claim 1, in which said portion C has a length greater than about 1.0 inches and said portion A has a length greater than about 1.0 inches.

15. The apparatus of claim 1, in which said portion C has a length greater than about 1.0 inches and less than about 2.5 inches, and said first portion A has a length greater than about 1.0 inches.

16. An apparatus for osteosynthesis of a mandible comprising:
an elongated plate having a plurality of apertures, said plate having a first portion and a central portion, each of said plurality of apertures within said first portion being disposed in relatively close spaced relationship, and each of said plurality of apertures within said central portion being disposed in relatively widely spaced relationship, wherein said plate between next adjacent apertures within said first portion has a first width, and said plate between next adjacent apertures within said central portion has a second width, said second width being substantially less than said first width.

17. The apparatus of claim 16, in which said first width is about 0.18 inches to about 0.32 inches, and said second width is about 0.12 inches to about 0.22 inches.

18. The apparatus of claim 17, in which each of said apertures has a diameter of about 0.10 to about 0.18 inches.

19. The apparatus of claim 17, in which each of said apertures has a diameter of about 0.16 inches.

20. The apparatus of claim 16, in which said first width is about 0.20 inches to about 0.24 inches, and said second width is about 0.12 inches to about 0.22 inches.

21. The apparatus of claim 16, in which said first width is about 0.20 inches and said second width is about 0.16 inches.

22. The apparatus of claim 16, in which said plate is more easily bent within said central portion than within said first portion.

23. The apparatus of claim 22, in which said plate, diametrically transverse across one of said apertures, has a first total cross-sectional area, and said plate, transverse between next adjacent apertures within said central portion, has a second cross-sectional area less than said first total cross-sectional area.

24. The apparatus of claim 22, in which said relatively close spaced relationship is less than about 0.34 inches center to center, and said relatively widely spaced relationship is greater than about 0.39 inches center to center.

25. The apparatus of claim 22, in which said relatively close spaced relationship is a distance of about 0.295 inches center to center between adjacent apertures, and said relatively widely spaced relationship is a distance of about 0.411 inches center to center between adjacent apertures.

26. The apparatus of claim 16, in which said relatively close spaced relationship is less than about 0.34 inches center to center, and said relatively widely spaced relationship is greater than about 0.39 inches center to center.

27. The apparatus of claim 16, in which said relatively close spaced relationship is a distance of about 0.295 inches center to center between adjacent apertures, and said relatively widely spaced relationship is a distance of about 0.411 inches center to center between adjacent apertures.

28. The apparatus of claim 16, in which said central portion has a length greater than about 1.0 inches and said first portion has a length greater than about 1.0 inches.

29. The apparatus of claim 16, in which said central portion has a length greater than about 1.0 inches and less than about 2.5 inches, and said first portion has a length greater than about 1.0 inches.

30. The apparatus of claim 22, in which said central portion has a length greater than about 1.0 inches and said first portion has a length greater than about 1.0 inches.

31. A method of surgically repairing a mandible comprising the steps of:
   a) providing an elongated plate having a plurality of apertures, said plate having a portion A and a portion B, each of said plurality of apertures within said portion A being disposed in relatively close spaced relationship, and each of said plurality of apertures within said portion B being disposed in relatively widely spaced relationship;
   b) providing a fastener having means for engaging said mandible and having means for engaging an aperture of said plate;
   c) securing said elongated plate to said mandible with said fastener; and
   d) bending said plate to substantially conform to said mandible such that said central portion overlies the symphysis of said mandible.

32. An apparatus for osteosynthesis of a mandible comprising:
   an elongated plate operable to be attached to the mandible, said elongated plate including:
      a single row of apertures disposed longitudinally along said elongated plate;
      a first portion having at least three apertures of said single row disposed therein;
      a second portion having at least another three apertures of said single row disposed therein;
      the distance between each next-adjacent aperture of said at least three apertures of said first portion being greater than the distance between each next-adjacent aperture of said at least another three apertures in said second portion.

33. An apparatus for osteosynthesis of a mandible having a symphysis and a posterior portion and adapted for fastening to the mandible by fasteners, said apparatus comprising:
   an elongated plate defined by a length greater than its width and having a first portion, a second portion, and a generally central portion intermediate said first and second portions; and
   a plurality of apertures disposed in a row along said length of said elongated plate and including at least three next-adjacent apertures in said first portion and at least three next-adjacent apertures in said second portion spaced closer together than at least three next-adjacent apertures in said central portion, said central portion operably appliable to the symphysis by the fasteners to allow unimpeded fastening of said elongated plate to the mandible.

34. An apparatus for osteosynthesis of a mandible having a symphysis and a posterior portion and adapted for fastening to the mandible by fasteners, said apparatus comprising:
   an elongated plate operable to be attached to the mandible, said elongated plate including:
      a single row of apertures disposed longitudinally along said elongated plate;
      a first portion having at least three next-adjacent apertures disposed therein;
      a pre-contoured second portion having at least another three next-adjacent apertures disposed therein;
      wherein said at least three next-adjacent apertures within said first portion are disposed in relatively closely spaced relationship and said at least another three next-adjacent apertures within said pre-contoured second portion are disposed in relatively widely spaced relationship, and wherein said second portion is operably appliable to the symphysis and said first portion is operably appliable to the posterior portion of the mandible, the relatively widely spaced relationship of said at least three next-adjacent apertures within said second portion allowing unimpeded fastening of said elongated plate to the mandible by the fasteners.

* * * * *